(12) United States Patent
Hasegawa et al.

(10) Patent No.: US 9,453,966 B2
(45) Date of Patent: Sep. 27, 2016

(54) OPTICAL PROBE

(71) Applicant: Sumitomo Electric Industries, Ltd., Osaka-shi (JP)

(72) Inventors: Takemi Hasegawa, Yokohama (JP); Kiyotaka Murashima, Yokohama (JP); Ryo Yamaguchi, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 14/699,754

(22) Filed: Apr. 29, 2015

(65) Prior Publication Data

US 2015/0331191 A1    Nov. 19, 2015

(30) Foreign Application Priority Data

May 16, 2014  (JP) ................................. 2014-102174

(51) Int. Cl.
| | |
|---|---|
| *G02B 6/26* | (2006.01) |
| *G02B 23/26* | (2006.01) |
| *G02B 23/24* | (2006.01) |
| *G02B 6/44* | (2006.01) |
| *A61B 5/00* | (2006.01) |

(52) U.S. Cl.
CPC ............... *G02B 6/26* (2013.01); *A61B 5/0066* (2013.01); *A61B 5/0084* (2013.01); *G02B 6/262* (2013.01); *G02B 6/44* (2013.01); *G02B 6/4433* (2013.01); *G02B 6/4478* (2013.01); *G02B 23/2423* (2013.01); *G02B 23/26* (2013.01); *A61B 2562/0233* (2013.01)

(58) Field of Classification Search
CPC .................................................. G02B 6/4433
USPC ................................................................ 385/38
See application file for complete search history.

(56) References Cited

U.S. PATENT DOCUMENTS

| | | | |
|---|---|---|---|
| 6,445,939 B1 | 9/2002 | Swanson et al. | |
| 6,891,984 B2 | 5/2005 | Petersen et al. | |
| 7,706,646 B2 * | 4/2010 | Wang | A61B 5/0062 362/572 |
| 7,813,609 B2 | 10/2010 | Petersen et al. | |
| 7,935,060 B2 * | 5/2011 | Schmitt | A61B 5/0066 600/467 |
| 8,724,941 B2 * | 5/2014 | Reever | A61B 18/24 385/31 |
| 2013/0331709 A1 * | 12/2013 | Le | G02B 6/32 600/478 |
| 2014/0212091 A1 * | 7/2014 | Hasegawa | A61B 5/0066 385/27 |

* cited by examiner

*Primary Examiner* — Sung Pak
(74) *Attorney, Agent, or Firm* — Venable LLP; Michael A. Sartori; F. Brock Riggs

(57) ABSTRACT

An optical probe has an optical fiber, a deflecting element, and a protective tube. The optical fiber includes a glass filament having a first diameter for transmitting light between the proximal and distal ends thereof and a resin layer for covering the filament except for the distal end thereof. The deflecting element is made of glass in a circular form having a second diameter larger than the first diameter, and it is connected with the optical fiber and has an end-face having a normal vector whose angle relative to the central axis is larger than the critical angle. The protective tube surrounds a portion of the optical fiber and the entire length of the deflecting element and is adhered to the side of a deflecting optical element, whereas the inside diameter of the part covering the optical fiber is smaller than that of the part covering the deflecting element.

2 Claims, 2 Drawing Sheets

OPTICAL PROBE

FIELD OF THE INVENTION

The present invention relates to an optical probe for optical measurement using Optical Coherence Tomography (OCT).

BACKGROUND ART

Optical coherence tomography (OCT) is known as a technique for measuring the intra-lumen tomographic structure of an object having a luminal form, such as a blood vessel. Also, as disclosed in U.S. Pat. No. 6,445,939B (Patent document 1), an optical probe inserted into the lumen of an object for performing such OCT measurement is known. The optical probe has a structure in which the tip (distal end) of a single mode optical fiber is connected to a graded index optical fiber having substantially the same diameter as the single mode optical fiber. By constituting the graded index optical fiber as a lens (GRIN lens) in such manner as the working distance is longer than 1 mm and the spot size is smaller than 100 μm, an object having an inner radius of more than 1 mm can be measured at spatial resolution finer than 100 μm according to the OCT method.

Furthermore, as disclosed in U.S. Pat. No. 6,891,984B (Patent document 2) and U.S. Pat. No. 7,813,609B (Patent document 3), by connecting an optical fiber, a GRIN lens, and a deflecting optical element altogether and by covering them with a transparent tube so that the air may be enclosed adjacent to the oblique end face of the deflecting optical element, it is made possible to make an optical probe which can reflect light in a lateral direction at the oblique end face. By rotating such optical probe, the tomographic structure of a luminal object, such as a blood vessel, can be measured by OCT.

SUMMARY OF THE INVENTION

Technical Problem

The object of the present invention is to provide an optical probe capable of stable performance even if it is bent.

Solution to Problem

An optical probe of the invention has an optical fiber, an optical connector, a deflecting optical element, a protective tube, and a jacketing tube. The optical fiber includes a glass filament in which the circular cross-section perpendicular to the central axis has a first diameter and which can transmit light between the proximal and distal ends thereof, and a resin layer which covers the side of the filament, whereas a portion of predetermined length from the distal end of the filament is not covered with the resin layer. The optical connector is connected with the optical fiber at the proximal end. The deflecting optical element is made of glass having a form in which the circular cross-section perpendicular to the central axis has a second diameter larger than the first diameter, and in which the refractive-index profile is such that the refractive index gradually decreases as it is distanced from the central axis in a cross-section perpendicular to the central axis, whereas a first end thereof is connected with an optical fiber at the distal end, and a second end face thereof has a normal vector in which the angle relative to the central axis is larger than the critical angle of total reflection. The protective tube surrounds a predetermined partial length of the optical fiber and the entire length of the deflecting optical element and is adhered to the side of a deflecting optical element, whereas the inside diameter of the part covering the optical fiber is smaller than the inside diameter of the part covering the deflecting optical element. The jacketing tube extends surrounding the optical fiber and can freely rotate relative to the optical fiber, the optical connector, and the deflecting optical element.

In the optical probe of the present invention, the diameter of the deflecting optical element may be 1.02 times to 1.10 times the diameter of the filament of the optical fiber.

Advantageous Effects of Invention

In the optical probe of the present invention, the tube can be prevented from coming off or being detached when a force is applied to the tube covering the GRIN lens, and the probe can stably be used in a state where it is bent.

DESCRIPTION OF EMBODIMENTS

Hereafter, embodiments of the present invention will be described in detail with reference to the accompanying drawings. In explanation of the drawings, the same mark is given to identical elements, and overlapping explanation will he omitted. The present invention is not limited to the embodiments and is shown by the claims, and it should be noted that all modifications which are equivalent to a claim in terms of meaning or scope are included in the scope of the invention.

As disclosed in Patent documents 1 to 3, with respect to optical probes of conventional technologies, the diameter of a GRIN lens and the diameter of an optical fiber are the same with each other. Therefore, it has been a problem that a probe tends to suffer from failures: for example, the tube comes off or the tube is detached from the GRIN lens because of a force applied to the tube covering the GRIN lens at the tip when the optical fiber and the GRIN lens are moved or rotated at a high speed in a state where the optical probe is bent. In particular, such failures easily occur when an optical probe is inserted in a bent blood vessel, because the optical probe is also bent accordingly, whereby the force applied to the tube becomes larger. These failures will degrade the quality of images obtained by OCT because in such cases unnecessary light reflection is caused on the side face of the GRIN lens of the optical probe or reflection efficiency is decreased at the end of the GRIN lens.

Figure 1:
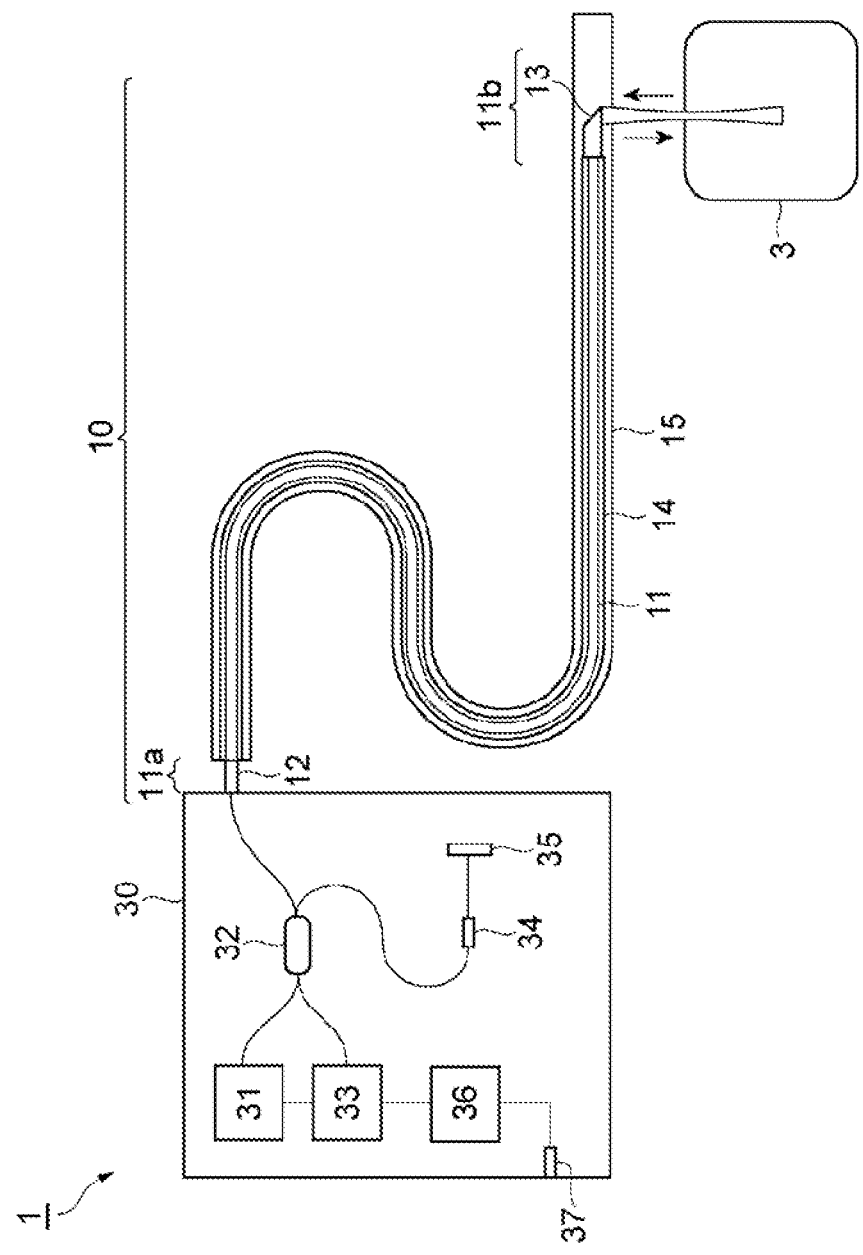
FIG. 1 is a schematic diagram showing an OCT system having an optical probe according to an embodiment of the present invention.

FIG. 1 is a schematic diagram showing an OCT system 1 having an optical probe 10 according to an embodiment of the present invention. The OCT system 1, which has an optical probe 10 and a measuring unit 30, obtains tomographic images of an object 3.

The optical probe 10 comprises: an optical fiber 11 for transmitting light between proximal end 11a and distal end 11b; an optical connector 12 connected with the optical fiber 11 at the proximal end 11a; a deflecting optical element 13 connected with the optical fiber 11 at the distal end 11b; a supporting tube 14 surrounding the optical fiber 11 and extending along the optical fiber 11; and a jacketing tube 15. The optical connector 12 is optically connected to a measuring unit 30.

The measuring unit 30 comprises: a light source 31 for generating light; an optical branch 32 for branching the light emitted from the light source 31 and outputting the branched light as illumination light and reference light; an optical detector 33 for detecting the light which has reached from the optical branch 32; a terminal 34 for outputting the reference light which has reached from the optical branch 32; a mirror 35 for reflecting, toward the terminal 34, the reference light which has been outputted from the terminal 34; an analyzing part 36 for analyzing the spectrum of the light detected by the optical detector 33; and an output port 37 for outputting results analyzed by the analyzing part 36.

The fight output from the light source 31 is branched into two by the optical branch 32 at the measuring unit 30 and emitted as illumination light and reference light. The illumination light output from the optical branch 32 enters into the proximal end 11a of the optical fiber 11 through the optical connector 12 and is guided by the optical fiber 11 so as to be emitted from the distal end 11b, and the light is irradiated to an object 3 through the deflecting optical element 13. The back reflected light which has arisen as a result of the illumination light being irradiated onto the object 3 enters into the distal end 11b of the optical fiber 11 through the deflecting optical element 13, and is guided by the optical fiber 11 so as to be emitted from the proximal end 11a, and the light is connected to the optical detector 33 through the optical connector 12 and the optical branch 32.

The reference light output from the optical branch 32 is emitted from the terminal 34 and reflected at the mirror 35 and connected to the optical detector 33 through the terminal 34 and the optical branch 32. The reference light and the light reflected back from the object 3 are combined by the optical branch 32 into interference light, which is detected by the optical detector 33. The spectrum of interference light is input into the analyzing part 36, wherein the spectrum of interference light is analyzed and the profile of the back reflection efficiency at each point inside the object 3 is calculated. The tomographic images of the object 3 are calculated on basis of the results of such calculation and outputted from the output port 37 as image signals.

Strictly speaking, as to a mechanism in which the illumination light emitted from the distal end 11b of the optical fiber 11 returns to the distal end 11b of the optical fiber 11 again via the object 3, there are reflection, refraction, and dispersion. However, such distinction is not essential to the present invention, and therefore, for the sake of concision, they are generically called as back-reflection in this specification.

At the measuring unit 30, the light source 31 generates broadband light which has a spectrum spreading continuously over the wavelength range of 1.6 µm to 1.8 µm. In this wavelength range, a lipid lesion has an absorption peak at a wavelength of 1.70 to 1.75 µm, and in this respect, it differs from a normal blood vessel. Therefore, when an object 3 containing lipid is measured, the spectrum of interference light is affected by absorption of lipid and exhibits significant attenuation at a wavelength of 1.70 to 1.75 µm as compared with a contiguous wavelength band.

Furthermore, since the spectrum of interference light has information on the tomographic structure of the object 3, it is possible to obtain information on the tomographic structure of the object 3 by conducting Fourier analysis of the spectrum by choosing a wavelength zone which is less influenced by absorption of a substance. By analyzing both tomographic structure information and lipid absorption information, it is made possible to calculate a tomographic image in which the lipid distribution is shown.

In such calculation, a plurality of lipid distributions may be derived from one spectrum, since a spectrum is influenced by both the absorption of lipid itself and the distribution of lipid. However, as generally known, the scattering intensity of lipid is lower as compared with the scattering intensity of a normal blood vessel, and therefore it is possible to obtain a true lipid distribution by choosing a solution which is most suitable to such known information.

The optical fiber 11 constituting the optical probe 10 is made of silica glass and has a length of 1 to 2 m. The optical fiber 11 is a filament having a circular cross-section. The optical fiber 11 has an attenuation of 2 dB or less, preferably 1 dB or less, in the wavelength range of 1.6 µm to 1.8 µm and has a cutoff wavelength of 1.53 µm or less, and operates in a single mode in the above-mentioned wavelength range. An optical fiber based on ITU-T G.652, G.654, or G.657 is suitable. In particular, an optical fiber based on ITU-T G.654 A or C is suitable, because it has an attenuation of 0.22 dB or less at the wavelength of 1.55 µm and has typically a pure silica glass core, and the noise due to nonlinear optical effects, such as a self-phase modulation can be reduced, since its nonlinear optical coefficient is low.

As the deflecting optical element 13, GRIN lens having a slant end-face is fusion-spliced to the distal end 11b of the optical fiber 11. The deflecting optical element 13 concentrates light emitted from the distal end 11b of the optical fiber 11 and deflects the light to a radial direction. The GRIN lens is made of silica glass, has a columnar form, and has an attenuation of 2 dB or less in the wavelength range of wavelength of 1.6 µm to 1.8 µm. The tip of the GRIN lens has a flat reflective surface having the normal vector at an angle beyond a total-reflection critical angle (43 degrees or more in the case of silica glass) relative to the axis. Therefore, at a position of the reflective surface, a cross-section perpendicular to the axis exhibits a partially circular form which lacks a part of the section.

If the angle of normal vector agree with 45 degrees, the reflected light reflected at the lens side will return to the optical fiber 11, resulting in noise. Therefore, it is desirable that the angle of normal vector be different from 45 degrees. On the other hand, if it is too large, the distance of light propagation will be prolonged, resulting in increase in optical loss. Therefore, it is desirable that the angle of normal vector be 46 to 51 degrees. As disclosed in Patent document 2, a hollow contiguous to a reflective surface can be formed by surrounding a lens with plastic tube, such as PET, and thereby total reflection of light can be caused at a reflective surface.

The optical fiber 11 is stored in the lumen of a supporting tube 14. The supporting tube 14 is fixed to an optical connector 12 and at least one portion of the optical fiber 11. As a result, if the optical connector 12 is rotated, the supporting tube 14 also rotates with it, transmitting the running torque to the optical fiber 11, and thereby the optical fiber 11, the deflecting optical element 13, and the supporting tube 14 will be rotated altogether. Therefore, it is possible to lessen the torque applied to the optical fiber 11 as compared with the torque where only the optical fiber 11 rotates, and thereby the optical fiber 11 can be prevented from fracturing due to torque.

It is desirable for the supporting tube 14 to have a thickness of 0.15 mm or more and Young's modulus of 100 to 300 GPa, which is substantially equivalent to stainless steel. The supporting tube 14 is not necessarily required to be connected in the circumferential direction and may have structure in which about 5 to 20 pieces of wires are twisted together so that its pliability may be adjusted.

The optical fiber 11, the deflecting optical element 13, and the supporting tube 14 are stored in the lumen of the jacketing tube 15, and they can be rotated in it. This will prevent an object 3 from being damaged by a rotating part contacting the object 3. The illumination light is emitted from the deflecting optical element 13, transmitted through the jacketing tube 15, and irradiated to the object 3. The jacketing tube 15, which is formed with transparent resins, such as PEBA (polyether block amide), Nylon, FEP (fluorinated ethylene-hexafluoopropylene copolymer), PFA (polyfluoroalkoxy), PTFE (polytetrafluoroethylene), and PET (polyethylene terephthalate), has a thickness of 10 to 50 μm and transparency like a transmission loss of 2 dB or less at a wavelength of 1.6 to 1.8 μm.

Figure 2:
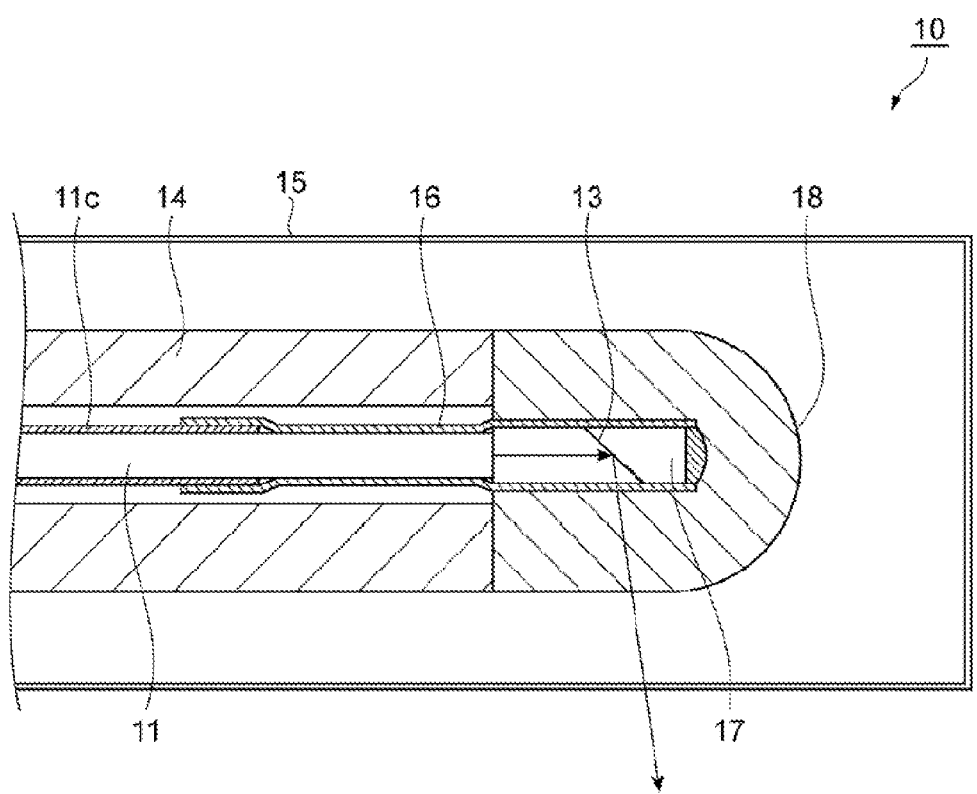
FIG. 2 is a sectional view of the distal end of an optical probe according to an embodiment of the present invention.

FIG. 2 is a sectional view of the distal end of an optical probe 10 of the present embodiment. A deflecting optical element (GRIN lens) 13 having a slant end-face is fusion spliced with the tip of the optical fiber 11. The optical fiber 11 is covered with a resin layer 11c made of polyimide or acrylate for mechanical protection, whereas the resin layer 11c is partially removed by a predetermined length at the tip for the purpose of fusion splicing with the GRIN lens 13.

A part of resin layer 11c of the optical fiber 11, the part where the resin layer 11c is removed, and the GRIN lens 13 are covered with a protective tube 16. The protective tube 16, which prevents the glass of the GRIN lens 13 and the optical fiber 11 from being damaged and losing strength, forms a hollow 17 which is contiguous to the reflective surface of the tip of the GRIN lens 13. It is desirable for the protective tube 16 to transmit near-infrared light and to stick to the GRIN lens 13 so as to restrain unnecessary reflection at the interface. Therefore, it is preferable to make the protective tube 16 with PET or PEBA having thermal contraction properties.

The optical fiber 11 has an outer diameter of 125 μm. On the other hand, the GRIN lens 13 has an outer diameter of 127 to 135 μm, which is 2 to 10% larger than the outer diameter of the optical fiber 11. This will increase adhesion between the GRIN lens 13 and the protective tube 16, Thus, when rotational or back-and-forth movement of the optical fiber 11 is performed in the optical probe 10, the protective tube 16 will be prevented from detaching from the GRIN lens 13, and occurrence of unnecessary reflection can he avoided.

The refractive power of the GRIN lens 13 varies according to the length of the GRIN lens 13. Therefore, it is important to manage the length of the GRIN lens 13 with sufficient reproducibility when manufacturing the optical probe 10. Usually, it is difficult to identify the connection interface between the optical fiber 11 and the GRIN lens 13 because they are both made of silica glass. However, if the optical fiber 11 and the GRIN lens 13 have outer diameters different from each other by 2 to 10% as in this embodiment, it is easy to identify their connection interface, and consequently the length of the GRIN lens 13 can easily be measured, so that the reproducibility of the optical properties of the optical probe 10 can be improved.

The GRIN lens 13 and the protective tube 16 are sealed with a transparent resin 18 for mechanical protection. As to the transparent resin 18, it is desirable to use an ultraviolet-curable epoxy or acrylate resin, since they can be easily molded. However, it is also possible to use a resin which is curable by heat or mixture of two kinds of liquid components.

What is claimed is:

1. An optical probe comprising:
   an optical fiber including a glass filament having a proximal end, a distal end, a first central axis, and a first circular cross-section being perpendicular to the first central axis and having a first diameter, the filament transmitting light between the proximal and distal ends, and a resin layer covering a side of the filament, whereas a portion of predetermined length from the distal end of the filament is not covered with the resin layer;
   an optical connector connected with the optical fiber at the proximal end;
   a deflecting optical element made of glass having a second central axis, a second circular cross-section, and a refractive index profile, the second circular cross-section being perpendicular to the second central axis and having a second diameter larger than the first diameter, the refractive-index profile being gradually decreases as distanced from the second central axis in the second circular cross-section, whereas a first end of the deflecting optical element is connected with the optical fiber at the distal end, and a second end of the deflecting optical element has a face having a normal vector, an angle between the normal vector and the second central axis being larger than a critical angle of total reflection;
   a protective tube surrounding a portion of predetermined length of the optical fiber and an entire length of the deflecting optical element, the protective tube adhering to a side of the deflecting optical element, whereas an inside diameter of a part covering the optical fiber is smaller than an inside diameter of a part covering the deflecting optical element; and
   a jacketing tube extending along and surrounding the optical fiber and capable of freely rotating relative to the optical fiber, the optical connector, and the deflecting optical element.

2. The optical probe according to claim 1, wherein the deflecting optical element has a diameter in a range of 1.02 times to 1.10 times a diameter of the filament of the optical fiber.

* * * * *